US009863861B2

United States Patent
Day, Jr. et al.

(10) Patent No.: US 9,863,861 B2
(45) Date of Patent: Jan. 9, 2018

(54) METHOD AND APPARATUS FOR PARTICLE SIZE DETERMINATION

(71) Applicants: Neil M. Day, Jr., Portola Valley, CA (US); Jing Dong, West Lafayette, IN (US)

(72) Inventors: Neil M. Day, Jr., Portola Valley, CA (US); Jing Dong, West Lafayette, IN (US)

(73) Assignee: Perfect Coffee, Inc., Oakland, CA (US)

( * ) Notice: Subject to any disclaimer, the term of this patent is extended or adjusted under 35 U.S.C. 154(b) by 0 days.

(21) Appl. No.: 14/194,154

(22) Filed: Feb. 28, 2014

(65) Prior Publication Data

US 2014/0241590 A1 Aug. 28, 2014

Related U.S. Application Data (60) Provisional application No. 61/770,743, filed on Feb. 28, 2013.

(51) Int. Cl.
*G06T 7/62* (2017.01)
*G06T 5/00* (2006.01)
(Continued)

(52) U.S. Cl.
CPC ..... *G01N 15/0205* (2013.01); *G01N 15/1468* (2013.01); *G06T 5/006* (2013.01);
(Continued)

(58) Field of Classification Search
CPC .......... G01N 15/0205; G01N 15/1468; G01N 33/02; G06T 2207/30204;
(Continued)

(56) References Cited

U.S. PATENT DOCUMENTS

2001/0041073 A1 11/2001 Sorek et al.
2002/0044682 A1* 4/2002 Weil ................. G06T 7/004
382/154

(Continued)

FOREIGN PATENT DOCUMENTS

EP 1031812 A2 8/2000

OTHER PUBLICATIONS

G. H. A. Janaka J. Kumara, Kimitoshi Hayano, and Keita Ogiwara, "Image Analysis Techniques on Evaluation of Particle Size Distribution of Gravel", Sep. 2012, Int. J. of Geomate, vol. 3, No. 1, pp. 290-297.*

(Continued)

*Primary Examiner* — Siamek Harandi
(74) *Attorney, Agent, or Firm* — Innovation Counsel LLP (57) ABSTRACT

A computer-implemented method of determining particle size and a computer-readable medium storing instructions to execute such a method are presented. The method entails obtaining an image of at least one particle and a calibration mark, wherein the particle and the calibration mark were captured using the same lens, correcting the image for distortion effects to generate a corrected image, wherein the same correction factor is applied to both the particle and the calibration mark, and determining a size of the particle using the corrected image. The method may be useful for obtaining the target size of coffee grounds that will produce the desired flavor. Coffee grounds may be sprinkled on a surface with the calibration mark and imaged with the calibration mark such that the correction factor for the calibration mark can be used to determine the particle size range of the coffee grounds.

16 Claims, 6 Drawing Sheets

(51) Int. Cl.
*G01N 15/02* (2006.01)
*G01N 15/14* (2006.01)
*G01N 33/02* (2006.01)

(52) U.S. Cl.
CPC ............. *G06T 7/62* (2017.01); *G01N 33/02* (2013.01); *G06T 2207/30128* (2013.01); *G06T 2207/30204* (2013.01); *G06T 2207/30208* (2013.01)

(58) Field of Classification Search
CPC ............. G06T 2207/30208; G06T 7/62; G06T 2207/30128; G06T 5/006
See application file for complete search history.

(56) References Cited

U.S. PATENT DOCUMENTS

| | | | |
|---|---|---|---|
| 2006/0187070 A1* | 8/2006 | Liang | B01D 46/008 340/607 |
| 2007/0058881 A1 | 3/2007 | Nishimura et al. | |
| 2012/0050488 A1* | 3/2012 | Cohen | G06T 5/006 348/46 |

OTHER PUBLICATIONS

David J. Graham; "A Transferable Method for the Automated Grain Sizing of River Gravels"; Water Resources Research, vol. 41, XP055119928, ISSN:0043-1397, Jul. 1, 2005.
Anonymous; "Communicating Grind Size Galla Coffee Blog", URL: http://www.gallacoffeeblog.co.uk/communicating-grind-size/; May 4, 2010.
Z. Zhang; "A Flexible New Technique for Camera Calibration", IEEE Transaction on Pattern Analysis and Machine Intelligence, vol. 22, No. 11, pp. 1330-1334, 2000.
Janaka J. Kumara et al.; "Image Analysis Technique on Evaluation of Particle Size Distribution of Gravel", XP055120157, URL: www.gi-j.com/serial%205/290-295-1261-kumara-sept-2012.pdf; pp. 290-297, Sep. 2012.
Paul Kippax et al.; "Optimizing the Particle Size of Ground Coffee"; XP055120160, URL: htttp://www.malvern.com/Assets/AR070305OptimisingParticledSozeGroundCoffee.pdf, Feb. 1, 2007.
Control Engineering Europe; "Analysis Goes on Line to Offer Real Time Measurement"; XP055120161. URL:http://www.malvern.com/Assets/AR121220MRK1885-01.pdf, Nov. 1, 2012.
PCT/US2014/019618 International Search Report dated Jun. 5, 2014.

* cited by examiner

METHOD AND APPARATUS FOR PARTICLE SIZE DETERMINATION

CROSS-REFERENCE TO RELATED APPLICATION(S)

This application claims the benefit of U.S. Provisional Application No. 61/770,743 filed on Feb. 28, 2013, which is incorporated by reference herein.

BACKGROUND

The inventive concept disclosed herein relates to a method and apparatus for determining the size distribution of particles.

Various methods for measuring the size distribution of small particles exist. These methods include using sieves, sedimentometry, laser diffraction, dynamic light scattering, and use of a microscope. Using sieves involves separating particles and measuring their size distribution based on varying mesh sizes of sieves. Sedimentometry, which is measurement using a sediment meter, measures the rate particles fall through a viscous medium, which rate is then correlated to particle size. Laser diffraction and dynamic light scattering use laser light directed at the particles. For laser diffraction, particle size distribution is determined based on the diffraction pattern of light scattered by the particles; for dynamic light scattering, particle size distribution is determined based on the changes in intensity of light scattered by particles in a solution. Microscopes can be used to directly measure particle sizes.

A problem with the above methods is that they are laborious and time-consuming, require specialized and expensive equipment such as lasers or an appropriate microscope, or both. Each method also typically requires trained personnel to use the equipment accurately. Such requirements limit these methods to industrial and laboratory applications. A method for measuring the size distribution of small particles that could be more readily used in a casual environment (e.g., in an average home) by individuals would be desirable.

SUMMARY

In one aspect, the inventive concept pertains to a computer-implemented method of determining a particle size. The method entails obtaining an image of at least one particle and a calibration mark, wherein the particle and the calibration mark were captured using the same lens, correcting the image for distortion effects to generate a corrected image, wherein the same correction factor is applied to both the particle and the calibration mark, and determining a size of the particle using the corrected image.

In another aspect, the inventive concept pertains to a computer-implemented method of achieving a desired particle size for coffee grounds. The method entails obtaining an image of coffee grounds dispersed on a surface having a calibration mark, wherein the particle and the calibration mark were captured using the same lens, correcting the image for distortion effects to generate a corrected image, wherein the same correction factor is applied to both the coffee grounds and the calibration mark, and determining a particle size range for the coffee grounds using the corrected image.

In yet another aspect, the inventive concept pertains to a computer-readable medium storing instructions for determining a particle size, wherein the instructions are to obtain an image of at least one particle and a calibration mark, wherein the particle and the calibration mark were captured using the same lens, correct the image for distortion effects to generate a corrected image, wherein the same correction factor is applied to both the particle and the calibration mark, and determine a size of the particle using the corrected image.

In yet another aspect, the inventive concept pertains to a computer-readable medium storing instructions for determining a particle size by obtaining an image of at least one particle using a lens, obtaining a measurement of the particle in the image, determining a lens distortion parameter and a perspective distortion parameter that are associated with the lens; and modifying the measurement of the particle by using the lens distortion parameter and the perspective distortion parameter.

DETAILED DESCRIPTION

A method for determining the size distribution of small particles using an image of such particles is disclosed. The method entails generating or otherwise obtaining an image (e.g., a bitmap) that includes the small particles and a calibration pattern, wherein the dimensions of the calibration pattern are known. The image may be produced, for example, using any conventional camera to image the small particles positioned on or around a calibration pattern. Where particle size is small (e.g., in the order of $10^{-6}$ inches), corrections are made to account for distortions caused by the camera lens.

In one embodiment of the method that is disclosed, particle size is determined using a calibration pattern that includes marks of known dimensions. The calibration pattern and the particles are imaged together, with the assumption that the same distortions will apply to both the calibration pattern and the particles. Using the known dimensions of the calibration pattern, a transformation is generated for removing the distortion effects and converting the image to a corrected image that is free of distortion effects. The transformation is then applied to determine particle size distribution from the corrected image.

Advantageously, any camera (or other device capable of producing a bitmap) can be used to record the bitmap, and specialized imaging or recording equipment is not required. Furthermore, because the calibration pattern and particles are recorded together in a single image, the camera, lens and other image parameters do not need to be known to correct for distortions and extract accurate particle sizes. Capturing the particles and the calibration pattern together in one image eliminates the need to record additional, separate calibration images to obtain a set of parameters to correct for distortions before recording the measurement image. In the method that is disclosed, the information necessary to accurately determine the sizes of the particles is embedded in a single image.

Figure 1:
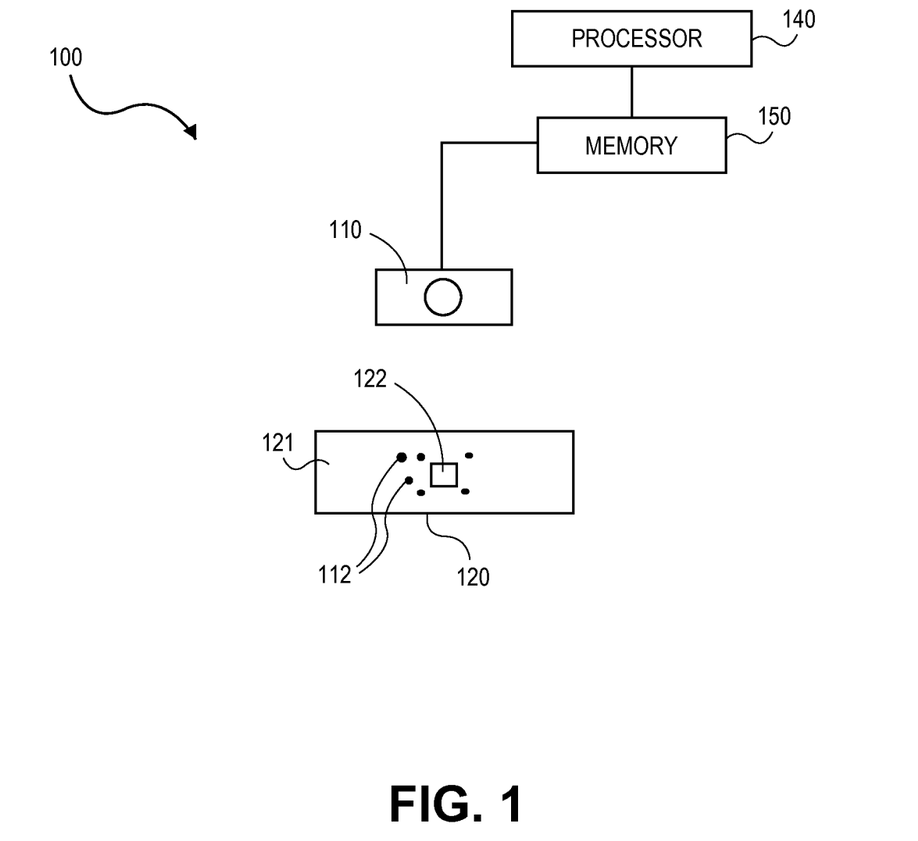
FIG. 1 is an embodiment of an apparatus for determining particle sizes.

FIG. 1 illustrates an embodiment of an apparatus 100 that may be used to implement the particle size determination technique disclosed herein. As shown, the apparatus 100 includes a camera 110 that is positioned to capture an image of particles 112 lying on a calibration pattern 120. As shown, the camera 110 stores the captured image in a memory 150 and communicates with a processor 140, either by direct connection or via a network. In one embodiment, the camera 110 may be part of a mobile device such as a smart phone, tablet, or a laptop. A "camera," as used herein, is intended to mean any imaging device capable of generating an electronic image (e.g., a bitmap) of physical objects using one or more lenses.

A stand [not shown] may be used to hold the camera 110, although the stand is not required and the camera 110 may be held by a person. The distance of the camera 110 from the calibration pattern 120 does not need to be known or specifically set, and should be in a range that allows the calibration pattern 120 and particles to be distinguished with appropriate pixel coverage of calibration marks and particles. The distance may be, for example, about 10 inches when using an iPhone® manufactured by Apple Inc.

Figure 2:
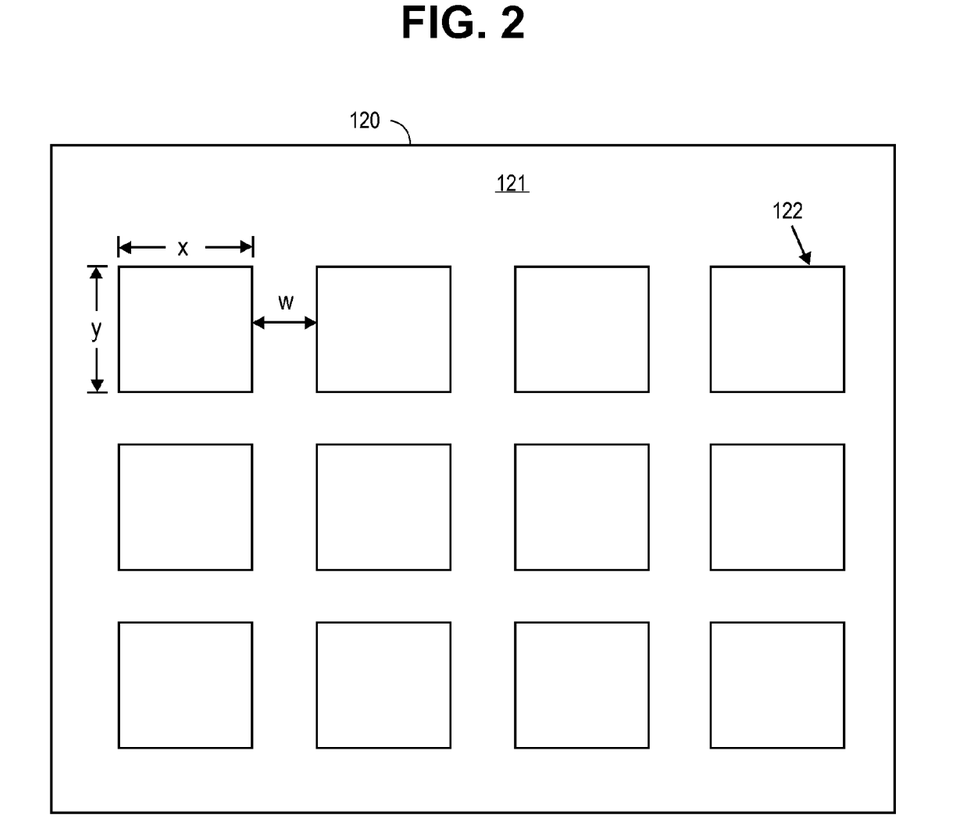
FIG. 2 is an example of a calibration pattern that may be used with the method of the disclosure.

FIG. 2 depicts an example embodiment of the calibration pattern 120. The calibration pattern 120 includes a background 121 and calibration marks 122. In the example calibration pattern 120 shown in FIG. 2, the calibration marks 122 are the outlines of squares having consistent dimensions x and y, which are drawn with lines of a substantially constant thickness and repeated at a consistent interval w in rows and columns. The dimensions of the calibration marks 122 are known (e.g., by measuring the physical pattern). The calibration marks 122 can be of any dimensions that provide enough information for producing a corrected image that allows accurate measurement in the desired particle size range.

The calibration pattern 120 is most useful if the main color or shade of the background 121 has a high contrast to the color of the particles to be measured and the color of the calibration marks 122. It is also useful to have the color of the calibration marks 122 be different than the color of the particles whose size is to be determined. For example, if the particles are brown or black, the background 121 may be white and the calibration patterns 122 may have a blue hue. In general, any material may be used for the calibration pattern 120, and it may be useful if the surface of the calibration pattern 120 is impervious to the material of the particles, so that the particles do not damage the calibration pattern 120. In one example, the calibration pattern 120 is a pattern printed on a sheet of paper and the particles are sprinkled on it. A digital image of the calibration pattern 120 may be obtained by the user and printed at home.

Figure 3:
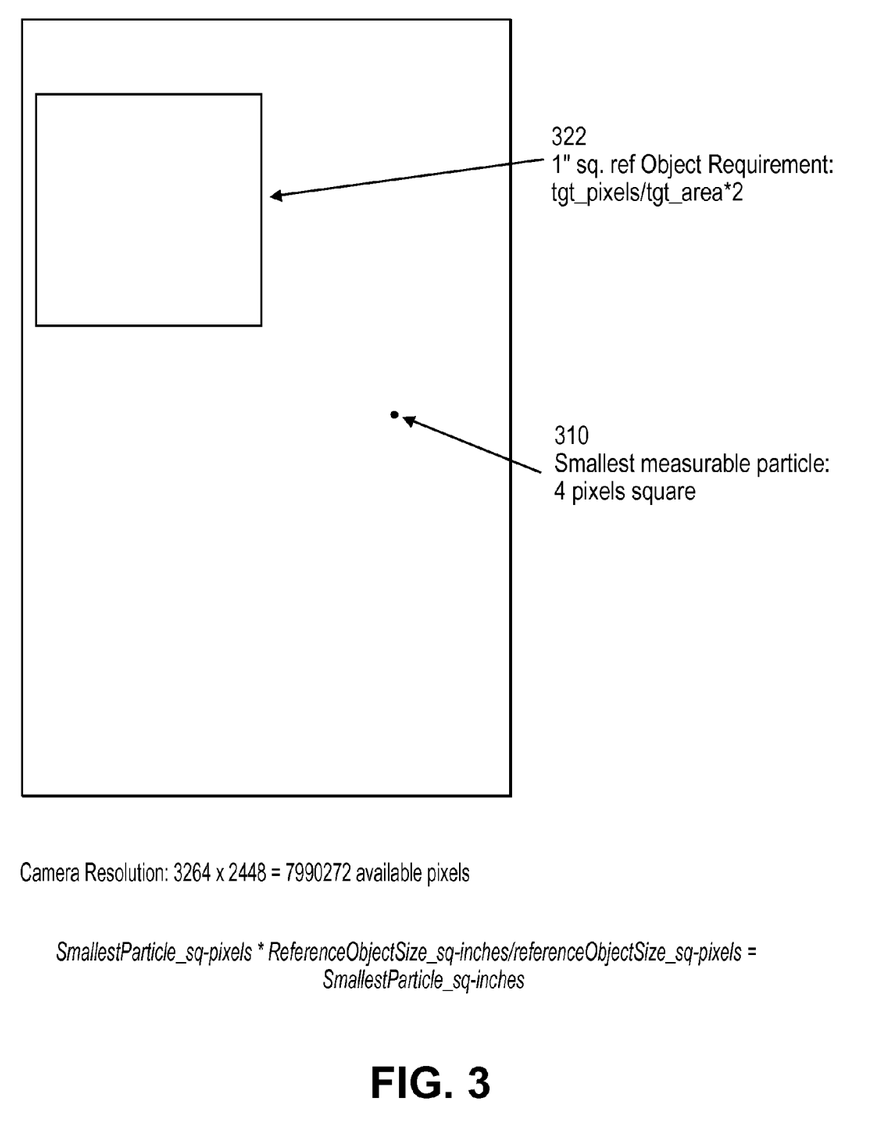
FIG. 3 illustrates example dimensions of a calibration pattern in relationship to particle size and pixel dimensions.

The smallest particle size that can be determined using the technique disclosed herein depends on a number of factors, one of which is the ratio between the smallest measurable object's pixel coverage and the calibration mark's pixel coverage. There also should be enough camera resolution to capture one or more calibration marks and enough particles of the sample to gather statistics. The camera that is part of an iPhone® that is currently available in the market would allow determination of particle size as small as $1\times10^{-6}$ inches. In one embodiment, the dimensions of the calibration marks 122 depend on the digital resolution of the camera and the size of the smallest particle to be measured. As shown for example in FIG. 3, for a camera having a resolution of 3264×2448 pixels, a square 310 of 2 pixels by 2 pixels is needed to measure a particle with a diameter of $25\times10^{-6}$ inches, and a calibration pattern 322 that is 400 pixels per side (i.e., surrounds an area of 160,000 pixels) is used. In the apparatus shown in FIG. 1, such a calibration pattern 120 would include calibration patterns 222 that are 1 inch square.

Patterns other than the repeating squares shown in FIG. 2 may be used for the calibration patterns 122. However, using a regular pattern that is mathematically easy to model, e.g., that includes orthogonal lines, for the calibration patterns 122 may simplify the processing of the recorded image. Additionally, as shown in FIG. 2, the calibrations mark 122 uses maximum use of the color that has a high contrast to the color of the particles whose size is being determined. A pattern such as a "checkerboard" pattern, for example, may not work as efficiently because half of the boxes would be dark and, where the particles are dark, too many of the particles would lie on the dark areas where there is not much contrast between the particles and the surface they are on.

Figure 4:
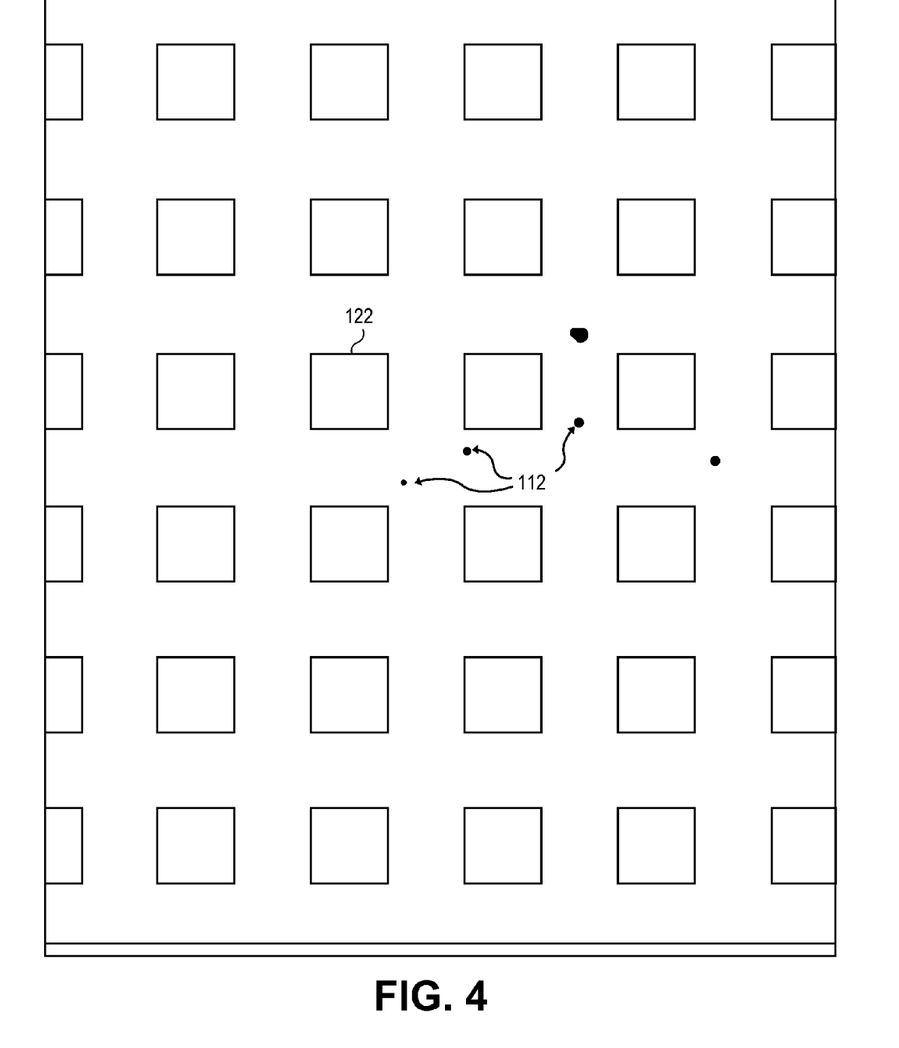
FIG. 4 illustrates an example of an image of sample particles on a calibration pattern.

FIG. 4 shows an example of particles 112 on the calibration pattern 120. To take the measurement, a sample of the particles to be measured is randomly placed (e.g., sprinkled) on the calibration pattern 120. It may be desirable to make the calibration marks 122 a complementary color to the particles 112 whose sizes are being determined. For example, if particles 112 are blue, the calibration marks 122 may be red.

Figure 5:
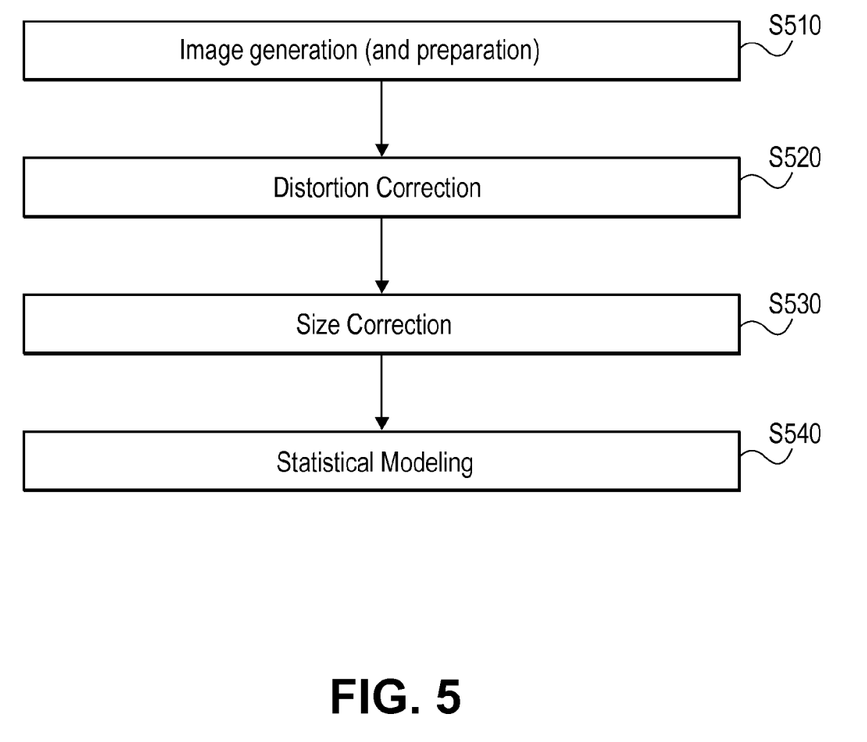
FIG. 5 is a flow diagram of an embodiment of a particle size determination method disclosed herein.
Figure 6:
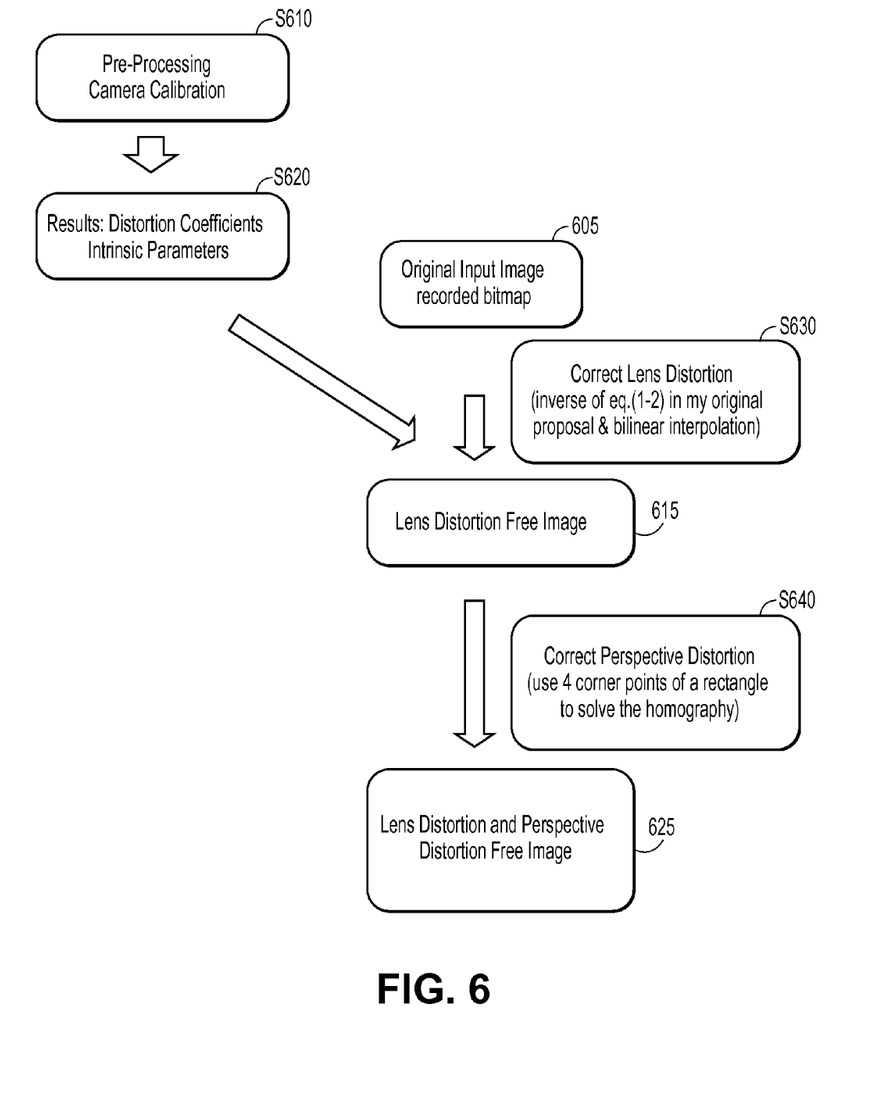
FIG. 6 is a flow diagram of a method for correcting lens and perspective distortions in an image.

The method of determining the particle size distribution from the image is described with respect to FIGS. 5 and 6.

FIG. 5 illustrates an embodiment of a method for determining particle size. After the particles to be measured are distributed on the calibration pattern 120, the camera 110 is used to capture a digital image (e.g. record a bitmap) of the particles on the calibration pattern 120 (step S510). The Image generation may include preparation of the image to facilitate object recognition, for example by applying image processing techniques (including, but not limited to noise reduction and/or thresholding and/or filtering) to improve the clarity/definition of the image. Any suitable noise reduction techniques may be used.

Any technology for capturing or generating two-dimensional or three-dimensional images may be used in step S510, including techniques that utilize photographic, ultrasound, x-ray, or radar. The inventive concept is not limited to any particular way of capturing the bitmap.

At step S520, the image of calibration pattern 120 is corrected to remove distortions. One of the problems of using imaging for determining particle size is that various distortions in the recorded image will lead to inaccuracies in the size determination. These distortions are particularly deleterious when trying to make accurate measurements of small particles, in the size ranges of, for example, $10^{-6}$ inches. Such distortions can be the result of imperfections in lens geometry or alignment, which may cause, for example, straight lines to be captured in the image as non-straight lines. Distortion can also be the result of perspective distortion, which occurs when the camera's optical axis is not perpendicular to the center of the object being imaged, causing parallel lines to appear non-parallel in the image. As particle sizes are determined using the dimensions of the calibration marks 122, distortion in the image of the calibration marks 122 will likely result in error in size determination. Hence, distortions in the calibration marks 122 are corrected before particle size determination is done. At the end of step S520, a "corrected image" is produced that includes the distortion-free calibration marks 122 and the original (uncorrected) image of the particles.

In one approach to removing distortions in step S520, calibration marks 122 are extracted from the image. A domain filtering technique may be used for this extraction. For example, where the calibration marks 122 are blue, a technique that uses a chroma range to extract patterns in the blue hue range may be used (the background 121 of the calibration pattern 120 is a different color from the marks 122). The result is a calibration mark object array that is built by extracting contours from the blue portions of the image. The calibration mark object array is used to generate a uniform scale that is useful for mapping the image, as in orthophotographs. This generation of a uniform scale is an ortho-transformation, which may be reused with the same calibration pattern 120 repeatedly once it is generated.

At step S530, particle sizes are determined using the corrected image of the calibration pattern 120. This process entails extracting the particles from the corrected image using domain filtering. For example, domain filtering may be accomplished using a chroma range to extract the particles that are known to be in the brown/black color range. A particle object array is generated by extracting contours of the particles from the processed image. Each element of the particle object array can then be measured to determine particles dimensions, for example the extent (diameter), area and circularity of each particle. From these measurements, a size distribution of the measured particles is obtained. In measuring the particle sizes, the calibration pattern acts as a dimensional reference.

As mentioned above, the dimensions of the calibration marks 122 in the physical world (as opposed to in the image) are known. Optionally, the accuracy of the calibration mark distortion correction used in S520 can be cross-checked by measuring the calibration marks in the corrected image and calculating the discrepancy from known sizes of the calibration marks 122 in the calibration pattern 120.

As step S540, the measurements of the particle object array are characterized. A size distribution histogram, an area distribution histogram, volume distribution histogram, minimum, maximum and standard deviations and distribution peak analysis may be used to determine a set of parameters that characterize the size and shape of the particles. A "set" of parameters, as used herein, is intended to mean at least one parameter.

In some cases, the particle size determination may be made with the objective of processing (e.g., grinding) the particles to achieve a desired size. In these cases, there may be a profile of target particles that is available, and the profile may be defined in terms of the set of parameters that is used in step S540. Based on a comparison of the measured parameters (result of step S540) against the profile of the target particles, one may determine what action needs to be taken to bring the two profiles closer. This determination may be made automatically by a processor or by a person. Where the determination is made automatically, the processor may indicate to an operator (e.g., visually and/or by sound) that further grinding would bring the measurement closer to the target profile.

One possible application of the particle size determination method described above is in preparing coffee, particularly in grinding coffee beans. It is known that the taste of a coffee drink is affected by several parameters, one of which is the fineness or the coarseness of the coffee grinds. A user who desires to make coffee of a certain flavor may obtain the profile of target coffee grinds that he knows would produce the flavor he wants when used with a specific setting in his coffee maker. Such user could sprinkle some coffee grinds on the calibration pattern 120 and use the above method to obtain the set of parameters that characterize his grinds, then compare the parameters to the target profile. For example, if the set of parameters indicate that measurement distribution for his grinds is centered on 0.035 inch and the target profile is for 0.0475 inch, the user would know that he ground the beans too fine and that he needs to restart with a coarser preparation.

Now, further details will be provided about the distortion correction step S520 of FIG. 5, and particularly about the generation of a transformation matrix for converting the original, distorted image to a distortion-free corrected image. The actual position of the calibration patterns is known from the physical, real-world calibration pattern. So, a comparison of the two (i.e., the actual position and the position in the image) can be used to determine a transformation matrix (or any other scalar) that converts the imaged calibration pattern back to the actual calibration pattern. This transformation matrix for the calibration pattern shows how to convert the image to real world measurements, and vice versa. The transformation matrix may be extrapolated across the set of pixels and applied to either the whole image or to a selected portion of the image in which, again using a chroma range extraction, just the particles are shown (obtained in step S530). After application of the transformation matrix to the image, a partially-corrected image that is less distorted (and perhaps substantially free of perspective or geometric distortions) is obtained. This approach generates a correction factor to each calibration mark 122 to correct for distortion.

FIG. 6 depicts another approach 600 for distortion correction. Unlike the first approach using the empirically-generated transformation matrix, this second approach entails correcting the image for lens distortion and perspective distortion. Using the calibration mark object array described above and regions of the image referenced by the calibration mark object array at steps S610 and S620, distortion coefficients are obtained. For example, a method described in the calibration method of Z. Zhang as described in "A flexible new technique for camera calibration," *IEEE Transaction on Pattern Analysis and Machine Intelligence*, 22(11):1330-1334, 2000, which is incorporated by reference herein, may be used. The method described in Zhang uses a checkerboard pattern to obtain calibration parameters that can be used in subsequent photographs. For the inventive concept disclosed herein, however, the calibration pattern 120 extracted from the image as described above is used. The calibration result obtained will include the lens distortion parameters as $k_1$ and $k_2$.

The technique proposed by Zhang uses the camera to observe a planar pattern shown at a few (at least two) different orientations. The pattern can be printed on a laser printer and attached to a "reasonable" planar surface (e.g., a hard book cover). Either the camera or the planar pattern may be moved and it is not necessary for the details of the motion to be known. The proposed approach lies between the photogrammetric calibration and self-calibration because 2D metric information is used rather than 3D or purely implicit one. Both computer simulation and real data have been used to test the proposed technique. The technique described herein advances 3D computer vision from laboratory environments to the real world.

Constraints on the camera's intrinsic parameters are provided by observing a single plane. A 2D point is denoted by $m=[u,v]^T$. A 3D point is denoted by $M=[X, Y, Z]^T$. The symbol denotes the augmented vector by adding 1 as the last element: $\tilde{m}=[u, v, 1]^T$ and $\tilde{M}=[X, Y, Z, 1]^T$. A camera is modeled by the usual pinhole: the relationship between a 3D point M and its image projection m is given by:

$$s\tilde{m}=A[Rt]\tilde{M} \quad \text{Equation (1)}$$

where s is an arbitrary scale factor; (R, t), called the extrinsic parameters, is the rotation and translation which relates the world coordinate system to the camera coordinate system; and A, called the camera intrinsic matrix, is given by:

$$A = \begin{bmatrix} \alpha & \gamma & u0 \\ 0 & \beta & v0 \\ 0 & 0 & 1 \end{bmatrix}$$

with ($u_0$, $v_0$) the coordinates of the principal point, $\alpha$ and $\beta$ the scale factors in image u and v axes, and $\gamma$ the parameter describing the skewness of the two image axes. The abbreviation $A^{-T}$ is used to represent $(A^{-1})^T$ or $(A^T)^{-1}$.

The model plane may be assumed as being on Z=0 of the world coordinate system. The $i^{th}$ column of the rotation matrix R will be denoted as $r_i$. From Equation (1), we have:

$$s\begin{bmatrix} u \\ v \\ 1 \end{bmatrix} = A[r_1 \ r_2 \ r_3 \ t]\begin{bmatrix} X \\ Y \\ 0 \\ 1 \end{bmatrix}$$

$$= A[r_1 \ r_2 \ t]\begin{bmatrix} X \\ Y \\ 1 \end{bmatrix}.$$

The symbol M is still used to denote a point on the model plane, but $M=[X, Y]^T$ since Z is equal to 0. In turn, $M=[X, Y, 1]^T$. Therefore, a model point M and its image m is related by a homography H:

$$s\tilde{m}=HM \text{ with } H=A[r_1 r_2 t]. \quad \text{Eq. (2)}$$

As is clear, the 3×3 matrix H is defined up to a scale factor.

Given an image of the model plane, a homography can be estimated. Denoting the homography by $H=[h_1 \ h_2 \ h_3]$, from Equation (2), we have $$[h_1 h_2 h_3]=\lambda A[r_1 r_2 t]$$

where $\lambda$ is an arbitrary scalar. Using the knowledge that $r_1$ and $r_2$ are orthonormal, the following constraints are obtained:

$$h_1^T A^{-T} A^{-1} h_2 = 0 \quad \text{Eq. (3)}$$

$$h_1^T A^{-T} A^{-1} h_1 = h_2^T A^{-T} A^{-1} h_2 \quad \text{Eq. (4)}$$

These are the two basic constraints on the intrinsic parameters, given one homography. Because a homography has 8 degrees of freedom and there are 6 extrinsic parameters (3 for rotation and 3 for translation), 2 constraints are obtained on the intrinsic parameters. The parameter $A^{-T}A^{-1}$ actually describes the image of the absolute conic. A geometric interpretation will now be provided.

The model plane, under the convention used herein, is described in the camera coordinate system by the following equation:

$$\begin{bmatrix} r_3 \\ r_3^T t \end{bmatrix}^T \begin{bmatrix} x \\ y \\ z \\ w \end{bmatrix} = 0,$$

where w=0 for points at infinity and w=1 otherwise. This plane intersects the plane at infinity at a line, and we can easily see that $$\begin{bmatrix} r1 \\ 0 \end{bmatrix} \text{ and } \begin{bmatrix} r2 \\ 0 \end{bmatrix}$$

are two particular points on that line. Any point on it is a linear combination of these two points, i.e., $$x_\infty = a\begin{bmatrix} r_1 \\ 0 \end{bmatrix} + b\begin{bmatrix} r_2 \\ 0 \end{bmatrix} = \begin{bmatrix} ar_1 + br_2 \\ 0 \end{bmatrix}.$$

Computing the intersection of the above line with the absolute conic, and knowing that by definition, the point $x_\infty$ (the circular point) satisfies $x_\infty^T x_\infty = 0$, i.e., $$(ar_1+br_2)^T(ar_1+br_2)=0, \text{ or } a^2+b^2=0.$$

The solution is b=±ai, where $i^2=-1$. That is, the two intersection points are $$x_\infty = a\begin{bmatrix} r_1 \pm ir_2 \\ 0 \end{bmatrix}.$$

Their projection in the image plane is then given, up to a scale factor, by $$\tilde{m}_\infty = A(r_1 \pm ir_2) = h_1 \pm ih_2.$$

Point $\tilde{m}_\infty$ is on the image of the absolute conic, described by $A^{-T} A^{-1}$. This gives $$(h_1 \pm ih_2)^T A^{-T} A^{-1} (h_1 \pm ih_2) = 0.$$

requiring that both real and imaginary parts be zero yields (3) and (4).

The details on how to effectively solve the camera calibration problem will now be provided. An analytical solution will be presented, followed by a nonlinear optimization technique based on the maximum likelihood criterion. Finally, both analytical and nonlinear solutions will be provided, taking lens distortion into account.

Consider the following Equation (5):

$$B = A^{-T} A^{-1}$$

$$\equiv \begin{bmatrix} B_{11} & B_{12} & B_{13} \\ B_{12} & B_{22} & B_{23} \\ B_{13} & B_{23} & B_{33} \end{bmatrix}$$

$$= \begin{bmatrix} \dfrac{1}{\alpha^2} & -\dfrac{\gamma}{\alpha^2\beta} & \dfrac{v_0\gamma - u_0\beta}{\alpha^2\beta} \\ -\dfrac{\gamma}{\alpha^2\beta} & \dfrac{\gamma^2}{\alpha^2\beta^2} + \dfrac{1}{\beta^2} & -\dfrac{\gamma(v_0\gamma - u_0\beta)}{\alpha^2\beta^2} - \dfrac{v_0}{\beta^2} \\ \dfrac{v_0\gamma - u_0\beta}{\alpha^2\beta} & -\dfrac{\gamma(v_0\gamma - u_0\beta)}{\alpha^2\beta^2} - \dfrac{v_0}{\beta^2} & \dfrac{(v_0\gamma - u_0\beta)^2}{\alpha^2\beta^2} + \dfrac{v_0^2}{\beta^2} + 1 \end{bmatrix}.$$

Noting that B is symmetric and defined by a 6D vector $$b=[B_{11},B_{12},B_{22},B_{13},B_{23},B_{33}]^T. \quad \text{Equation (6)}$$

Let the ith column vector of H be $hi=[h_{i1}, h_{i2}, h_{i3}]^T$. Then, we have $$h_i^T B h_j = v_{ij}^T b \quad \text{Equation (7)}$$

with $$v_{ij}=[h_{i1}h_{j1},h_{i1}h_{j2}+h_{i2}h_{j1},h_{i2}h_{j2},h_{i3}h_{j1}+h_{i1}h_{j3},h_{i3}h_{j2}+h_{i2}h_{j3},h_{i3}h_{j3}]^T.$$

Therefore, the two fundamental constraints (3) and (4), from a given homography, can be rewritten as 2 homogeneous equations in b, as shown below in Equation (8):

$$\begin{bmatrix} v_{12}^T \\ (v_{11}-v_{22})^T \end{bmatrix} b = 0. \quad \text{Equation (8)}$$

If n images of the model plane are observed, by stacking n such equations as (8), the result can be expressed as:

$$Vb=0, \quad \text{Equation (9)}$$

where V is a 2n×6 matrix. If n≥3, generally, a unique solution b defined up to a scale factor is obtained. If n=2, the skewless constraint γ=0, i.e., [0, 1, 0, 0, 0, 0]b=0, can be imposed and added as an additional equation to Equation (9). (If n=1, two camera intrinsic parameters, e.g., α and β, may be solved assuming $u_0$ and $v_o$ are known (e.g., at the image center) and γ=0. The solution to Equation (9) is well-known as the eigenvector of $V^T V$ associated with the smallest eigenvalue (equivalently, the right singular vector of V associated with the smallest singular value).

Once b is estimated, values in camera intrinsic matrix A can be calculated. Once A is known, the extrinsic parameters for each image may be computed. Using Equation (2), for example, the following may be obtained:

$$r_1 = \lambda A^{-1} h_1$$

$$r_2 = \lambda A^{-1} h_2$$

$$r_3 = r_1 \times r_2$$

$$t = \lambda A^{-1} h_3$$

with $\lambda = 1/\|A^{-1}h_1\| = 1/\|A^{-1}h_2\|$. Due to the presence of noise in data, the so-computed matrix R=[r1, r2, r3] does not satisfy the properties of a rotation matrix.

Suppose there are n images of a model plane and m points on the model plane. Suppose also that the image points are corrupted by independent and identically distributed noise. The maximum likelihood estimate can be obtained by minimizing the following functional:

$$\Sigma_{i=1}^n \Sigma_{j=1}^m \|m_{ij}-\hat{m}(A,R_i,t_i,M_j)\|^2, \quad \text{Value (10)}$$

where $\hat{m}(A, R_i, t_i, M_j)$ is the projection of point $M_j$ in image i, according to Equation (2). A rotation R is parameterized by a vector of 3 parameters, denoted by r, which is parallel to the rotation axis and whose magnitude is equal to the rotation angle. R and r are related by the Rodrigues formula. Minimizing Value (10) is a nonlinear minimization problem, which may be solved with the Alevenberg-Marquardt Algorithm. It uses an initial guess of A, {Ri, $t_i$|i=1 . . . n} which can be obtained using the technique described above.

The solutions above do not consider lens distortion of a camera. However, a desktop camera usually exhibits significant lens distortion, especially radial distortion. Now, first two terms of radial distortion will be discussed. It is likely that the distortion function is dominated by the radial components, and especially by the first term.

Let (u, υ) be the ideal (distortion-free) pixel image coordinates, and (ŭ, ῠ) the corresponding real observed image coordinates. The ideal points are the projection of the model points according to the pinhole model. Similarly, (x, y) and (x̆, y̆) are the ideal (distortion-free) and real (distorted) normalized image coordinates.

$$\breve{x}=x+x[k_1(x^2+y^2)+k_2(x^2+y^2)^2]$$

$$\breve{y}=y+y[k_1(x^2+y^2)+k_2(x^2+y^2)^2]$$

where k1 and k2 are the coefficients of the radial distortion. The center of the radial distortion is the same as the principal point. From $$\breve{u}=u+(u-u_0)[k_1(x^2+y^2)+k_2(x^2+y^2)^2] \quad \text{Equation (11)}$$

$$\breve{v}=v+(v-v_0)[k_1(x^2+y^2)+k_2(x^2+y^2)^2] \quad \text{Equation (12)}$$

Estimating Radial Distortion by Alternation.

As the radial distortion is expected to be small, one would expect to estimate the other five intrinsic parameters, using the technique described above reasonably well by simply ignoring distortion. One strategy is then to estimate k1 and k2 after having estimated the other parameters, which will give the ideal pixel coordinates (u, υ). Then, from Equations (11) and (12), we have two equations for each point in each image:

$$\begin{bmatrix} (u-u_0)(x^2+y^2) & (u-u_0)(x^2+y^2)^2 \\ (v-v_0)(x^2+y^2) & (v-v_0)(x^2+y^2)^2 \end{bmatrix} \begin{bmatrix} k_1 \\ k_2 \end{bmatrix} = \begin{bmatrix} \breve{u}-u \\ \breve{v}-v \end{bmatrix}.$$

Given m points in n images, we can stack all equations together to obtain in total 2 mn equations, or in matrix form as Dk=d, where k=[$k_1$, $k_2$]$^T$. The linear least-squares solution is given by $$k=(D^T D)^{-1} D^T d. \quad \text{Equation (13)}$$

Once $k_1$ and $k_2$ are estimated, one can refine the estimate of the other parameters by solving Equation (10) with $\hat{m}(A, R_i, t_i, M_j)$ replaced by Equations (11) and (12). We can alternate these two procedures until convergence.

The convergence of the above alternation technique may be slow. A natural extension to Equation (10) is to estimate the complete set of parameters by minimizing the following functional:

$$\Sigma_{i=1}^n \Sigma_{j=1}^m \|m_{ij}-\hat{m}(A,k_1,k_2,R_i,t_i,M_j)\|^2, \quad \text{Value (14)}$$

where $\hat{m}$ (A, $k_1$, $k_2$, $R_i$, $t_i$, $M_j$) is the projection of point Mj in image i according to Equation (2), followed by distortion according to Equations (11) and (12). This is a nonlinear minimization problem, which is solved with the Levenberg-Marquardt Algorithm. A rotation is again parameterized by a 3-vector r, as disclosed above. An initial guess of A and {$R_i$, ti|i=1 . . . n} can be obtained using the technique described above. An initial guess of k1 and k2 can be obtained with the radial distortion solutions described above, or simply by setting them to 0.

At step S630, the lens distortion parameters $k_1$ and $k_2$ are then used on the original image 605 to obtain an image 615 that is corrected for lens distortion. Alternatively, instead of using the image, a particle object array that describes the particle's geometries, may be corrected. The lens distortion parameters k1 and k2 are used to correct the image for lens distortion using the following equations (15) and (16).

Let ($x_{correct}$, $y_{correct}$) represent the correct locations in the image if there were no distortion due to the lens. Then:

$$x_{distorted} = x_{correct} + (x_{correct} - u_0)(k_1 r^2 + k_2 r^4) \qquad (15)$$

$$y_{distorted} = y_{correct} + (y_{correct} - v_0)(k_1 r^2 + k_2 r^4) \qquad (16)$$

where $r^2 = (x_{correct} - u_0)^2 + (y_{correct} - v_0)^2$, and $u_0$ and $v_0$ are principal points (i.e., the intersection points of the camera optical axis and image plane).

The lens distortion can then be corrected by warping the recorded bitmap with a reverse distortion. For each pixel in the corrected image, its corresponding location is mapped in the distorted image using equation (15) and (16) above. The section below titled Geometric Image Transformations describes how the two-dimensional image coordinates and the three-dimensional world coordinates are related by a camera's intrinsic parameters (e.g., focal lens, principal points, distortion coefficients) and extrinsic parameters (rotation and translation matrix). For each integer pixel coordinates in the destination (corrected bitmap), trace back to the source (recorded bitmap) and find the corresponding float coordinates, using the surrounding integer pixels to interpolate the float coordinates. Bilinear interpolation may be used in this process.

In Summary, the lens-distortion correction procedure proposed here, part of which incorporate Zhang's technique, is as follows:

1) Print a pattern and attach it to a planar surface;
2) Take a few images of the model plane under different orientations by moving either the plane or the camera;
3) Detect the feature points in the images;
4) Estimate the five intrinsic parameters and all the extrinsic parameters using the closed-form solution provided above;
5) Estimate the coefficients of the radial distortion by solving the linear least-squares Equation (13);
6) Refine all parameters by minimizing Value (14); at this point, k1 and k2 have assigned values;
7) Use Equations (15) and (16) below and the width and height of the lens distorted image, to find the height and width of the image that is free of lens distortion. Use a scalar to keep the two images at the same width, and scale height accordingly; and
8) For each pixel in the image that is free of lens distortion, find its corresponding location using Equations (15) and (16) in the image that has lens distortion, and apply Shepard's interpolation of nearby neighbors in the distorted image to get the color information for the corrected image.

At step S640, correction for perspective distortion may be achieved using the four corner points of a rectangular calibration mark to solve the homology H using the following process:

Suppose we have a point in world coordinates $$\begin{bmatrix} x^{world} \\ y^{world} \end{bmatrix}$$

and we write this in homogenous coordinates as $$\begin{bmatrix} kx^{world} \\ ky^{world} \\ k \end{bmatrix}.$$

Similarly, the corresponding point in image coordinates is $$\begin{bmatrix} x^{img} \\ y^{img} \end{bmatrix},$$

and we write this in homogenous coordinates as $$\begin{bmatrix} k'x^{img} \\ k'y^{img} \\ k' \end{bmatrix}.$$

The relationship between these two can be expressed in the following equation $$\begin{bmatrix} k'x^{img} \\ k'y^{img} \\ k' \end{bmatrix} = H \begin{bmatrix} kx^{world} \\ ky^{world} \\ k \end{bmatrix}$$

where $$H = \begin{bmatrix} H_{11} & H_{12} & H_{13} \\ H_{21} & H_{22} & H_{23} \\ H_{31} & H_{32} & 1 \end{bmatrix}$$

is the Homography we want to solve.

Expanding both sides of the equation using matrix multiplication, we get:

$$k'x^{img} = k(H_{11}x^{world} + H_{12}y^{world} + H_{13})$$

$$k'y^{img} = k(H_{21}x^{world} + H_{22}y^{world} + H_{23})$$

$$k' = k(H_{31}x^{world} + H_{32}y^{world} + 1)$$

Plug in the third equation to the first two, we get two equations from this pair of points:

$$x^{img} = H_{11}x^{world} + H_{12}y^{world} + H_{13} - H_{31}x^{img}x^{world} - H_{32}x^{img}y^{world}$$

$$y^{img} = H_{21}x^{world} + H_{22}y^{world} + H_{23} - H_{31}y^{img}x^{world} - H_{32}y^{img}y^{world}$$

Since there are eight unknowns in H, we need 4 pairs of points to solve H. We write the eight equations in matrix form:

$$\begin{bmatrix} x_0^{img} \\ y_0^{img} \\ x_1^{img} \\ y_1^{img} \\ x_2^{img} \\ y_2^{img} \\ x_3^{img} \\ y_3^{img} \end{bmatrix} = $$

$$\begin{bmatrix} x_0^{world} & y_0^{world} & 1 & 0 & 0 & 0 & -x_0^{img}x_0^{world} & -x_0^{img}y_0^{world} \\ 0 & 0 & 0 & x_0^{world} & y_0^{world} & 1 & -y_0^{img}x_0^{world} & -y_0^{img}y_0^{world} \\ x_1^{world} & y_1^{world} & 1 & 0 & 0 & 0 & -x_1^{img}x_1^{world} & -x_1^{img}y_1^{world} \\ 0 & 0 & 0 & x_1^{world} & y_1^{world} & 1 & -y_1^{img}x_1^{world} & -y_1^{img}y_1^{world} \\ x_2^{world} & y_2^{world} & 1 & 0 & 0 & 0 & -x_2^{img}x_2^{world} & -x_2^{img}y_2^{world} \\ 0 & 0 & 0 & x_2^{world} & y_2^{world} & 1 & -y_2^{img}x_2^{world} & -y_2^{img}y_2^{world} \\ x_3^{world} & y_3^{world} & 1 & 0 & 0 & 0 & -x_3^{img}x_3^{world} & -x_3^{img}y_3^{world} \\ 0 & 0 & 0 & x_3^{world} & y_3^{world} & 1 & -y_3^{img}x_3^{world} & -y_3^{img}y_3^{world} \end{bmatrix} \begin{bmatrix} H_{11} \\ H_{12} \\ H_{13} \\ H_{21} \\ H_{22} \\ H_{23} \\ H_{31} \\ H_{32} \end{bmatrix}$$

Thus, for each image suffers from the projective distortion, we pick four points in this image, and given the world coordinates of these four points, we are able to solve H.

The "k" in the above equation is a scalar for the homogeneous representation of the two-dimensional coordinates, different from the lens coefficients k1, k2. Four points (e.g., four corners where the shape is rectangular) of multiple calibration marks 122 may be used to account for nonuniformity of distortions. As shown in FIG. 6, the starting point for perspective correction in this approach is not the original image, but the corrected image where lens distortion effects have been removed. The homography H is determined using four points from a set of calibration marks identified in the image corrected for lens distortion, and then is applied to the corrected image to determine a bitmap 625 (the corrected, or true-size, bitmap) that has been corrected for both lens and perspective distortion.

A perspective distortion usually occurs when the camera's optical axis is not perpendicular to the center of the object. Using the image of particles captured on a grid-patterned background, multiple (e.g., five) pairs of orthogonal lines in the scene may be used to find the homography to correct the perspective distortion. This correction will often make parallel lines in the physical world also parallel in the image, orthogonal lines in the physical world also orthogonal in the image, squares in the physical world have unit aspect ratio in the image, and/or circles in the physical world circular in the image.

To summarize the perspective distortion correction process detailed above, the process entails the following steps:
1) Obtain a calibration pattern containing orthogonal lines of known dimensions, disperse particles on the calibration pattern, and capture the image using the same lens;
2) Choose multiple (e.g., five) pairs of orthogonal lines on the image;
3) Solve the homography H between the projection-distorted image and the image that is free of projection distortion;
4) Use H and the width and height of the projection-distorted image to find the height and width of the image that is free of projection distortion. Use a scalar to keep the two images at the same width, and scale height accordingly; and
5) For each pixel in the image that is free of projection distortion, find its corresponding location in the projection-distorted image to get the color information for the correct image.

The lens distortion correction and the projection distortion correction maybe tested separately and cascaded, so that Shepard's interpolation may only be done once.

The method illustrated in FIGS. 5 and 6 may be implemented in a processing device. As discussed with respect to FIG. 1, once the camera 110 captures the image, the data processing of the image can occur using a processor directly connected to the camera 110 or the image data may be transmitted to a separate processor.

Geometric Image Transformations

This section will now talk about some known image transformation functions that may be used to correct and manipulate the image of the particle. More specifically, the functions in this section perform various geometrical transformations of 2D images. They do not change the image content but deform the pixel grid and map this deformed grid to the destination image. In fact, to avoid sampling artifacts, the mapping is done in the reverse order, from destination to the source. That is, for each pixel (x,y) of the destination image, the functions compute coordinates of the corresponding "donor" pixel in the source image and copy the pixel value:

$$\text{dst}(x,y) = \text{src}(f_x(x,y), f_y(x,y))$$

In case the forward mapping is specified as $(g_x, g_y)$: src→dst, the functions described below first compute the corresponding inverse mapping $(f_x, f_y)$: dst→src and then use the above formula.

The actual implementations of the geometrical transformations, from the most generic Remap and to the simplest and the fastest Resize, need to solve two main problems with the above formula.

Extrapolation of non-existing pixels. Similarly to the filtering functions, for some (x,y), either one of $f_x(x,y)$, or $f_y(x,y)$, or both of them may fall outside of the image. In this case, an extrapolation method needs to be used. OpenCV provides the same selection of extrapolation methods as in the filtering functions. In addition, it provides the method Border_Transparent. This means that the corresponding pixels in the destination image will not be modified at all.

Interpolation of pixel values. Usually $f_x(x,y)$ and $f_y(x,y)$ are floating-point numbers. This means that $(f_x, f_y)$ can be either an affine or perspective transformation, or radial lens distortion correction, and so on. So, a pixel value at fractional coordinates needs to be retrieved. In the simplest case, the coordinates can be rounded to the nearest integer coordinates and the corresponding pixel can be used. This is called a nearest-neighbor interpolation. However, a better result can be achieved by using more sophisticated interpolation methods, where a polynomial function is fit into some neighborhood of the computed pixel ($f_x(x,y)$, $f_y(x,y)$), and then the value of the polynomial at ($f_x(x,y)$, $f_y(x,y)$) is taken as the interpolated pixel value. In OpenCV, you can choose between several interpolation methods, some of which will be described below.

Get Rotation Matrix 2D

This function calculates an affine matrix of 2D rotation. Some parameters used for this process are as follows:
- center—Center of the rotation in the source image.
- angle—Rotation angle in degrees. Positive values mean counter-clockwise rotation (the coordinate origin is assumed to be the top-left corner).
- scale—Isotropic scale factor.
- map_matrix—The output affine transformation, 2×3 floating-point matrix.

The function calculates the following matrix:

$$\begin{bmatrix} \alpha & \beta & (1-\alpha)\cdot center\cdot x - \beta \cdot center \cdot y \\ -\beta & \alpha & \beta \cdot center \cdot x + (1-\alpha) \cdot center \cdot y \end{bmatrix}$$

where
- $\alpha$=scale·cos angle,
- $\beta$=scale·sin angle

The transformation maps the rotation center to itself. If this is not the target, the shift should be adjusted.

Get Affine Transform

This function calculates the affine transform from 3 corresponding points. Some parameters used for this process are as follows:
- src—Coordinates of triangle vertices in the source image.
- dst—Coordinates of the corresponding triangle vertices in the destination image.
- mapMatrix—Pointer to the destination 2×3 matrix The function calculates the 2×3 matrix of an affine transform so that:

$$\begin{bmatrix} x'_i \\ y'_i \end{bmatrix} = map\_matrix \cdot \begin{bmatrix} x_i \\ y_i \\ 1 \end{bmatrix}$$

where $dst(i) = (x'_i, y'_i)$, $src(i) = (x_i, y_i)$, $i = 0, 1, 2$

Get Perspective Transform

This function calculates a perspective transform from four pairs of the corresponding points. Some parameters used for this process are as follows:
- src—Coordinates of quadrangle vertices in the source image.
- dst—Coordinates of the corresponding quadrangle vertices in the destination image.
- mapMatrix—Pointer to the destination 3×3 matrix [A/b]

The function calculates a matrix of a perspective transforms so that:

$$\begin{bmatrix} t_i x'_i \\ t_i y'_i \\ t_i \end{bmatrix} = map\_matrix \cdot \begin{bmatrix} x_i \\ y_i \\ 1 \end{bmatrix}$$

where $dst(i) = (x'_i, y'_i)$, $src(i) = (x_i, y_i)$, $i = 0, 1, 2, 3$

Get Quadrangle SubPix

This process retrieves a pixel rectangle from an image with sub-pixel accuracy. Some parameters used for this process are as follows:
- src—source image.
- dst—extracted quadrangle
- mapMatrix—the transformation 2×3 matrix [A/b]

This function extracts pixels from src at sub-pixel accuracy and stores them to dst as follows:

$$dst(x, y) = src(A_{11}x' + A_{12} \cdot y' + b_1, A_{21}x' + A_{22} \cdot y' + b_2)$$

where $$x' = x - \frac{(width(dst) - 1)}{2},$$

$$y' = y - \frac{(height(dst) - 1)}{2}$$

and $$mapMatrix = \begin{bmatrix} A11 & A12 & b1 \\ A21 & A22 & b2 \end{bmatrix}$$

The values of the pixels at non-integer coordinates are retrieved using bilinear interpolation. When the function needs pixels outside of the image, it uses replication border mode to reconstruct the values. Every channel of multiple-channel images is processed independently.

GetRectSubPix

This function retrieves the pixel rectangle from an image with sub-pixel accuracy.
- src—Source image.
- Dst—extracted rectangle
- Center—floating point coordinates of the extracted rectangle center within the source image. The center must be inside the image.

This function extracts pixels from src:

dst(x,y)=src(x+center·x−(dst·cols−1)*0.5,y+center·y−(dst·rows−1)*0.5)

where the values of the pixels at non-integer coordinates are retrieved using bilinear interpolation. Every channel of multiple-channel images is processed independently. While the rectangle center must be inside the image, parts of the rectangle may be outside. In this case, the replication border mode is used to get pixel values beyond the image boundaries.

Log Polar

This function remaps an image to a log-polar space.
- src—Source image
- dst—Destination image
- center—The transformation center; where the output precision is maximal
- M—Magnitude scale parameter.
- flags—A combination of interpolation methods and the following optional flags:
    - CV_WARP_FILL_OUTLIERS fills all of the destination image pixels. If some of them correspond to outliers in the source image, they are set to zero
    - CV_WARP_INVERSE_MAP See below This function transforms the source image using the following transformation:

Forward transformation (CV_WARP_INVERSE_MAP is not set):

$$dst(\varphi,\rho)=src(x,y)$$

Inverse transformation (CV_WARP_INVERSE_MAP is set):

$$dst(x,y)=src(\varphi,\rho)$$

where $$\rho=M\cdot\log\sqrt{x^2+y^2}, \varphi=a\tan(y/x)$$

The function emulates the human "foveal" vision and can be used for fast scale and rotation invariant template matching, for object tracking and so forth. The function cannot operate in-place.

Remap

This function applies a generic geometrical transformation to the image.
  src—Source image.
  dst—Destination image.
  mapx—the map of x-coordinates.
  mapy—the map of y-coordinates.
  flags—Interpolation method (see resize ( )). The method INTER_AREA is not supported by this function.
  fillval—a value used to fill outliers This function transforms the source image using the specified map:

$$dst(x,y)=src(map_x(x,y),map_y(x,y))$$

where values of pixels with non-integer coordinates are computed using one of available interpolation methods. $map_x$ and $map_y$ can be encoded as separate floating-point maps in $map_1$ and $map_2$ respectively, or interleaved floating-point maps of (x, y) in $map_1$, or fixed-point maps created by using ConvertMaps function. The reason one might want to convert from floating to fixed-point representations of a map is that they can yield much faster (~2x) remapping operations. In the converted case, $map_1$ contains pairs (cvFloor(x), cvFloor(y)) and $map_2$ contains indices in a table of interpolation coefficients. This function cannot operate in-place.

Resize

This function resizes an image.
  src—input image.
  dst—output image; it has the size dsize (when it is non-zero) or the size computed from src.size( ) fx, and fy; the type of dst is the same as of src.
  interpolation—interpolation method:
    INTER_NN—a nearest-neighbor interpolation
    INTER_LINEAR—a bilinear interpolation (used by default)
    INTER_AREA—resampling using pixel area relation. It may be a preferred method for image decimation, as it gives moire'-free results. But when the image is zoomed, it is similar to the INTER_NN method.
    INTER_CUBIC—a bicubic interpolation over 4×4 pixel neighborhood
    INTER_LANCZOS4—a Lanczos interpolation over 8×8 pixel neighborhood To shrink an image, it will generally look best with INTER_AREA interpolation, whereas to enlarge an image, it will generally look best with INTER_CUBIC (slow) or INTER_LINEAR (faster but still looks OK).

WarpAffine

This function applies an affine transformation to an image.
  src—source image.
  dst—destination image.
  mapMatrix—2×3 transformation matrix.
  flags—a combination of interpolation methods and the optional flags:
    CV_WARP_FILL_OUTLIERS—fills all of the destination image pixels; if some of them correspond to outliers in the source image, they are set to fillval
    CV_WARP_INVERSE_MAP indicates that matrix is inversely transformed from the destination image to the source and thus, can be used directly for pixel interpolation. Otherwise, the function finds the inverse transform from mapMatrix.
  Fillval—a value used to fill outliers The function warpAffine transforms the source image using the specified matrix:

$$dst(x,y)=src(M_{11}x+M_{12}y+M_{13}, M_{21}x+M_{22}y+M_{23})$$

when the flag WARP_INVERSE_MAP is set. Otherwise, the transformation is first inverted with InvertAffineTransform and then put in the formula above instead of M. The function cannot operate in-place.

$$dst(x,y) = src\left(\frac{M_{11}x + M_{12}y + M_{13}}{M_{31}x + M_{32}y + M_{33}}, \frac{M_{21}x + M_{22}y + M_{23}}{M_{31}x + M_{32}y + M_{33}}\right)$$

The function is similar to GetQuadrangleSubPix but they are not exactly the same. WarpAffine requires input and output image have the same data type, has larger overhead (so it is not quite suitable for small images) and can leave part of destination image unchanged. While GetQuadrangleSubPix may extract quadrangles from 8-bit images into floating-point buffer, has smaller overhead and always changes the whole destination image content. The function cannot operate in-place.

WarpPerspective

This function applies a perspective transformation to an image. Parameters useful for this function include the following:
  Src—Source image
  Dst—Destination image
  mapMatrix—3×3 transformation matrix
  flags—A combination of interpolation methods and the following optional flags:
    CV_WARP_FILL_OUTLIERS—fills all of the destination image pixels; if some of them correspond to outliers in the source image, they are set to fillval
  CV_WARP_INVERSE_MAP—indicates that matrix is inversely transformed from the destination image to the source and, thus, can be used directly for pixel interpolation. Otherwise, the function finds the inverse transform from mapMatrix
  filval—A value used to fill outliers This function transforms the source image using the specified matrix:

$$\begin{bmatrix} x' \\ y' \end{bmatrix} = mapMatrix \cdot \begin{bmatrix} x \\ y \\ 1 \end{bmatrix}$$

if CV_WARP_INVERSE_MAP is not set $$\begin{bmatrix} x \\ y \end{bmatrix} = mapMatrix \cdot \begin{bmatrix} x' \\ y' \\ 1 \end{bmatrix}$$

otherwise
Note that the function cannot operate in-place.

While the embodiments are described in terms of a method or technique, it should be understood that the disclosure may also cover an article of manufacture that includes a non-transitory computer readable medium on which computer-readable instructions for carrying out embodiments of the method are stored. The computer readable medium may include, for example, semiconductor, magnetic, opto-magnetic, optical, or other forms of computer readable medium for storing computer readable code. Further, the disclosure may also cover apparatuses for practicing embodiments of the inventive concept disclosed herein. Such apparatus may include circuits, dedicated and/or programmable, to carry out operations pertaining to embodiments.

Examples of such apparatus include a general purpose computer and/or a dedicated computing device when appropriately programmed and may include a combination of a computer/computing device and dedicated/programmable hardware circuits (such as electrical, mechanical, and/or optical circuits) adapted for the various operations pertaining to the embodiments.

What is claimed is:

1. A computer-implemented method of determining a particle size, comprising:
   providing an apparatus including a background and a lens that is fixed at a predetermined distance above the background;
   obtaining an image of a calibration mark physically positioned on the background by using the lens;
   placing a plurality of particles on the background;
   obtaining an image of the particles on the background, wherein the particles and the calibration mark were captured using the same lens;
   correcting the image for distortion effects to generate a corrected image, wherein the same correction factor is applied to both the particles and the calibration mark;
   characterizing size and shape of the particles with a set of parameters by using the corrected image, wherein the set of parameters comprises one or more of size distribution, area distribution, and volume distribution;
   comparing the set of parameters with a target particle profile; and
   determining a type of grinding action that brings the set of parameters closer to the target particle profile.

2. The method of claim 1, wherein the calibration mark comprises straight lines extending in perpendicular directions.

3. The method of claim 1, wherein the image includes a plurality of particles randomly positioned with respect to the calibration mark.

4. The method of claim 1, wherein the image is a bitmap.

5. The method of claim 1, wherein the determining of the size comprises separating a first portion of the image that includes the particle from a second portion of the image that includes the calibration mark in the image.

6. The method of claim 5, wherein the separating comprises using chroma range extraction.

7. The method of claim 1, wherein correcting the image for distortion effects comprises:
   comparing a known actual dimension of the calibration mark with the dimension of the calibration mark obtained from the image;
   generating a correction factor based on the comparing;
   obtaining a measurement of the particle in the image; and
   modifying the measurement of the particle by using the correction factor.

8. The method of claim 1, wherein correcting the image for distortion effects comprises correcting at least one of lens distortion and perspective distortion.

9. A computer-implemented method of achieving a desired particle size for coffee grounds, comprising:
   providing an apparatus including a background and a lens that is fixed at a predetermined distance above the background;
   obtaining an image of a calibration mark on the background;
   placing coffee grounds on the background;
   obtaining an image of the coffee grounds dispersed on the background by using the same lens;
   correcting the image for distortion effects to generate a corrected image, wherein the same correction factor is applied to both the coffee grounds and the calibration mark; and
   characterizing size and shape of the coffee grounds with a set of parameters by using the corrected image, wherein the parameters comprise one or more of size distribution, area distribution, and volume distribution;
   comparing the set of parameters with a target particle size profile; and
   determining a type of grinding action that brings the set of parameters closer to the target particle profile.

10. The method of claim 9, wherein the image is a bitmap.

11. The method of claim 9, wherein the determining of the particle size comprises:
    separating the image into a first portion that includes the coffee grounds and a second portion that includes the calibration mark;
    computing a correction factor for the calibration mark by comparing the physical measurements of the calibration mark with the calibration mark in the second portion of the image; and
    applying the correction factor for the calibration mark to the first portion of the image to obtain a corrected particle size for the coffee grounds.

12. The method of claim 9, wherein the determining of the particle size comprises:
    correcting the image for lens distortion; and
    correcting the image for perspective distortion.

13. A non-transitory computer-readable medium storing instructions for determining a particle size, the instructions comprising:
    obtaining an image of a plurality of particles and a calibration mark with an apparatus that includes a background and a lens that is fixed at a predetermined distance above the background, wherein the particles are placed on the background;
    correcting the image for distortion effects to generate a corrected image, wherein the same correction factor is applied to both the particles and the calibration mark;
    characterizing size and shape of the particles with a set of parameters by using the corrected image, wherein the set of parameters comprises one or more of size distribution, area distribution, and volume distribution;

comparing the set of parameters with a target particle profile; and determining a type of grinding action that brings the set of parameters closer to the target particle profile.

14. The non-transitory computer-readable medium of claim 13, wherein the image is a bitmap.

15. The non-transitory computer-readable medium of claim 13, wherein the determining of the particle size comprises:

separating the image into a first portion that includes the particle and a second portion that includes the calibration mark;

computing a correction factor for the calibration mark by comparing the physical measurements of the calibration mark with the calibration mark in the second portion of the image; and applying the correction factor for the calibration mark to the first portion of the image to obtain a corrected particle size for the coffee grounds.

16. The non-transitory computer-readable medium of claim 13, wherein the determining of the particle size comprises:

correcting the image for lens distortion; and correcting the image for perspective distortion.

* * * * *